(12) United States Patent
Kaji et al.

(10) Patent No.: US 7,144,392 B2
(45) Date of Patent: Dec. 5, 2006

(54) MEDICAL EMBOLIZATION ELEMENT AND METHOD OF EMBOLIZING TUBULAR ORGAN

(75) Inventors: Hinako Kaji, Hachiouji (JP); Kunihide Kaji, Hachiouji (JP)

(73) Assignee: Olympus Corporation, Tokyo (JP)

( * ) Notice: Subject to any disclaimer, the term of this patent is extended or adjusted under 35 U.S.C. 154(b) by 614 days.

(21) Appl. No.: 10/198,778

(22) Filed: Jul. 19, 2002

(65) Prior Publication Data
US 2003/0018351 A1    Jan. 23, 2003

(30) Foreign Application Priority Data
Jul. 19, 2001 (JP) .............................. 2001-220005

(51) Int. Cl.
*A61M 31/00* (2006.01)
*A61M 29/00* (2006.01)
(52) U.S. Cl. ...................... 604/516; 606/191; 606/200
(58) Field of Classification Search ........ 604/514–516; 606/108, 191, 200–233; 128/207.15, 207.16
See application file for complete search history.

(56) References Cited
U.S. PATENT DOCUMENTS

| 5,669,924 | A | * | 9/1997 | Shaknovich | ............... 623/1.11 |
| 6,258,100 | B1 | * | 7/2001 | Alferness et al. | ............ 606/108 |
| 6,287,290 | B1 | * | 9/2001 | Perkins et al. | ............... 604/516 |
| 6,398,775 | B1 | * | 6/2002 | Perkins et al. | ............... 604/514 |
| 6,679,264 | B1 | * | 1/2004 | Deem et al. | ............ 128/207.16 |

FOREIGN PATENT DOCUMENTS
WO     WO 98/48706     11/1998

\* cited by examiner

*Primary Examiner*—Vy Q. Bui
(74) *Attorney, Agent, or Firm*—Scully, Scott, Murphy & Presser PC

(57) ABSTRACT

To provide a medical embolization element for embolizing the internal cavity of a tubular organ of a subject, for example, a medical embolization element for embolizing a bronchus during treatment of lung emphysema. A placing object being placed in a bifurcation of the tubular cavity includes a first embolization portion capable of airtightly sealing a first branch tubular cavity of the bifurcation, a second embolization portion capable of embolizing another second branch tubular cavity of the bifurcation, and a locking portion being locked to an edge portion of the junction portion between the first and second branch tubular cavities. Other than the above described placing object, a placing object having a balloon, a placing object shaped like cap to be attached on the tip of an endoscope, a placing object expandable in the tubular organ, and a placing object solidifies in the tubular organ are disclosed.

2 Claims, 12 Drawing Sheets

FIG. 4
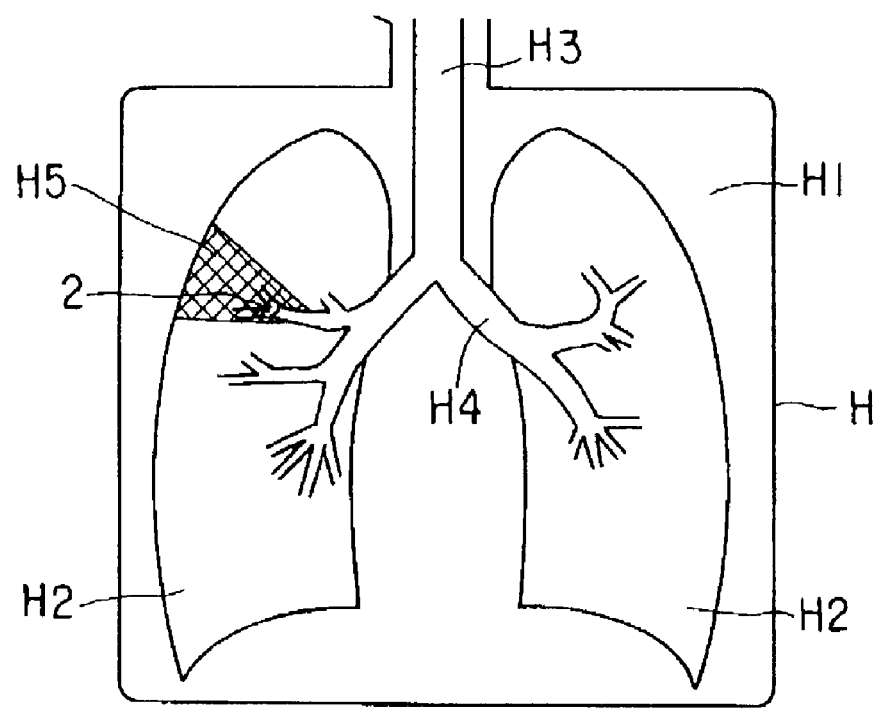
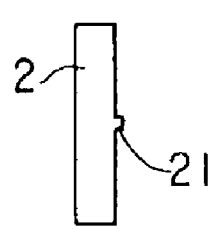
FIG. 5A
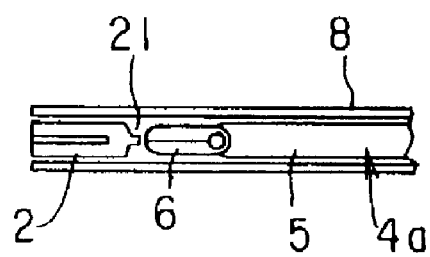
FIG. 5B

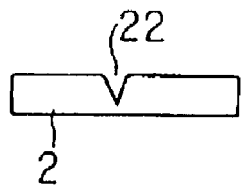
FIG. 6A
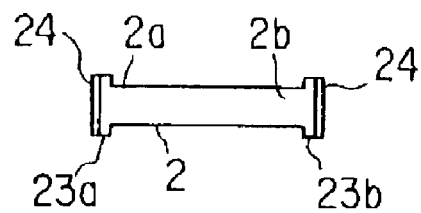
FIG. 6B
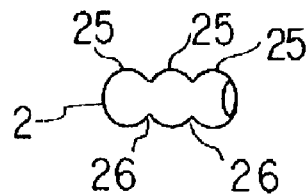
FIG. 6C
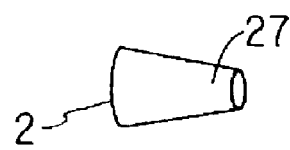
FIG. 6D
FIG. 7
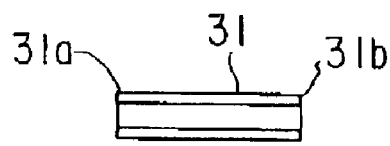
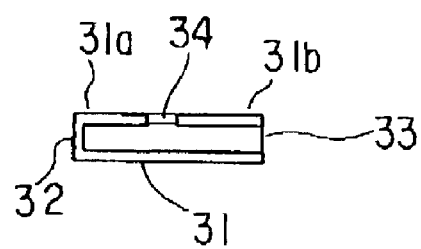
FIG. 8A
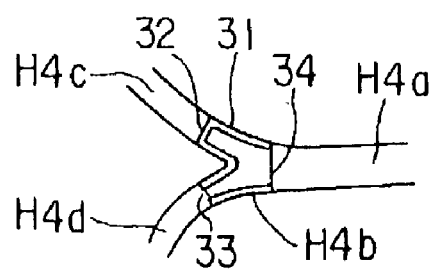
FIG. 8B

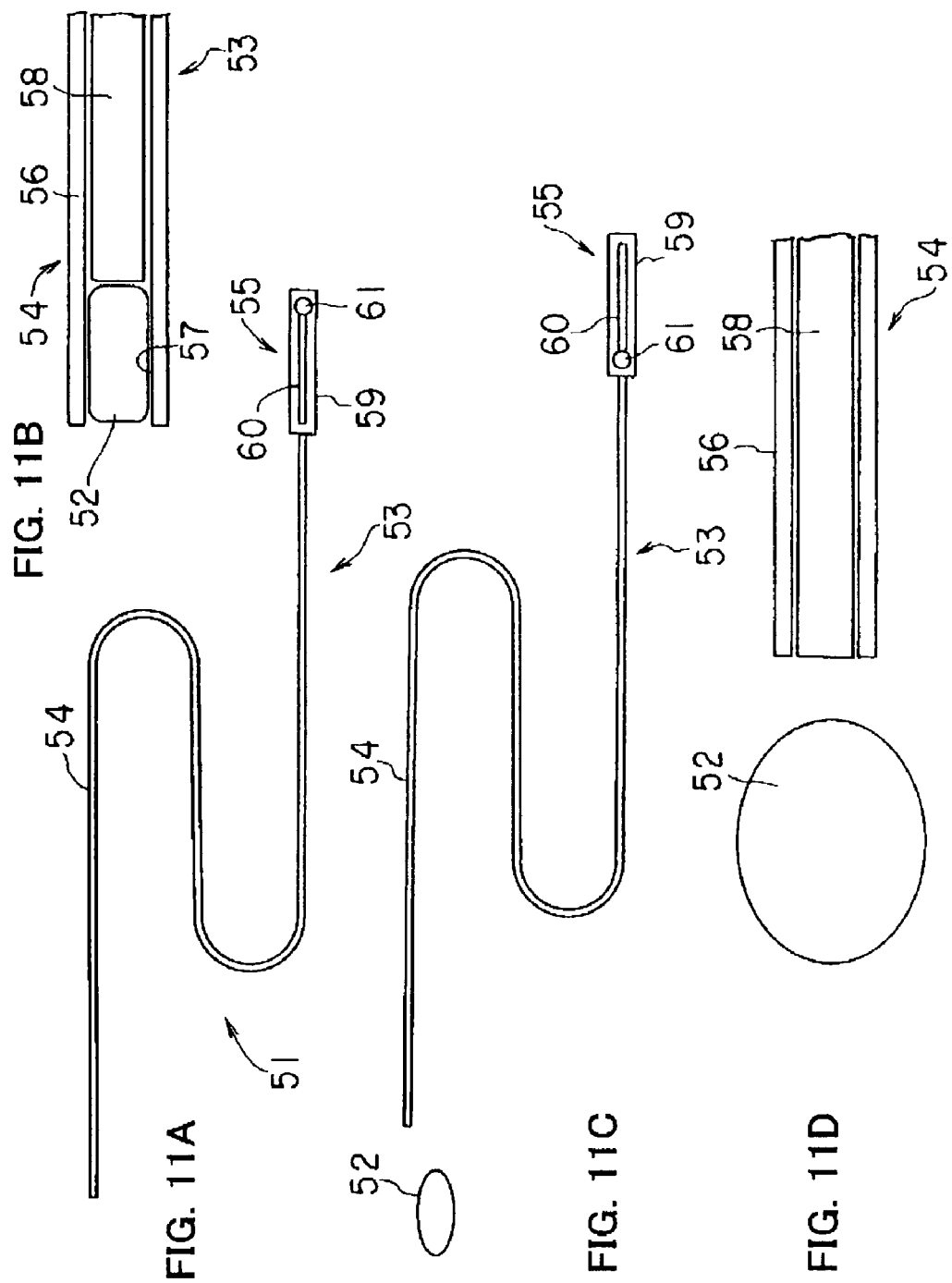

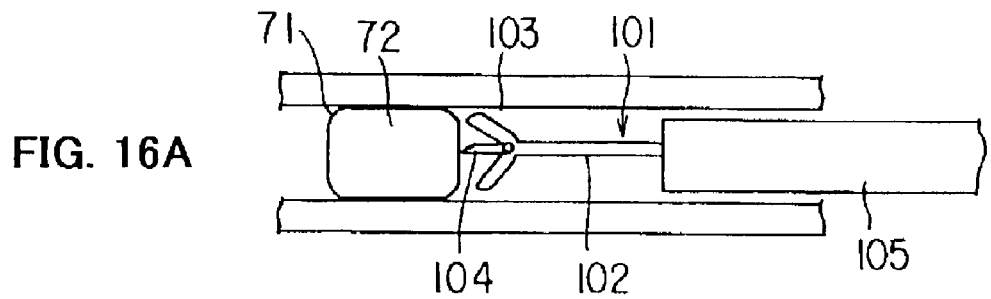
FIG. 16A
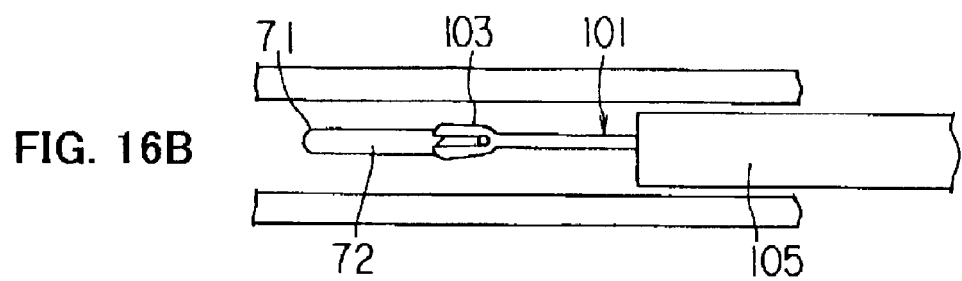
FIG. 16B
FIG. 17
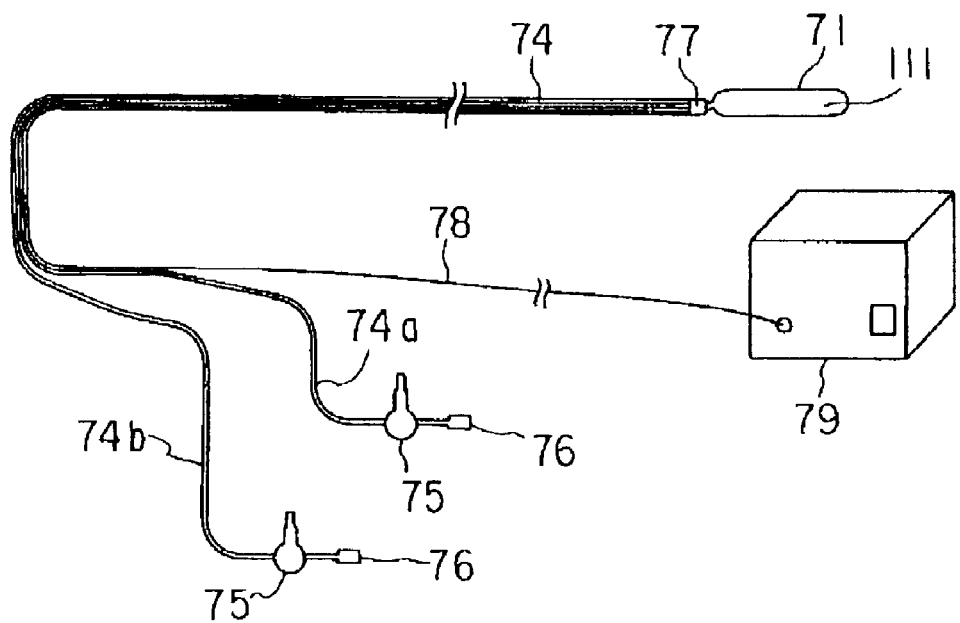

FIG. 20
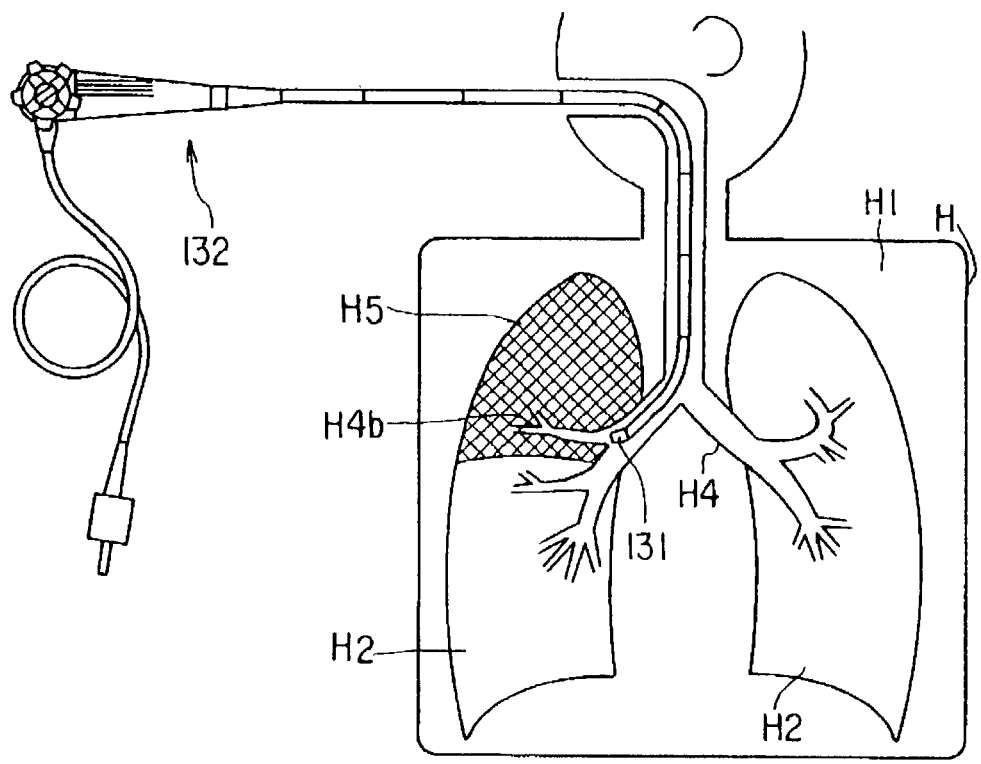
FIG. 21A
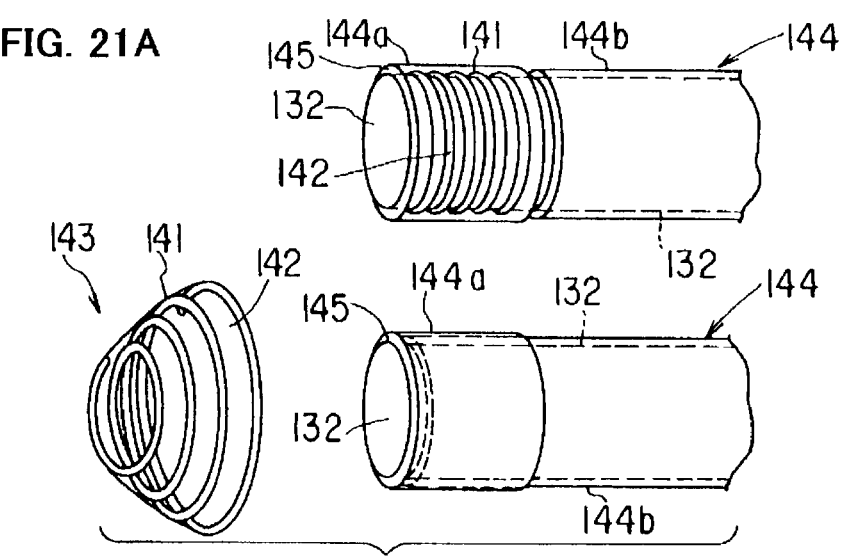
FIG. 21B

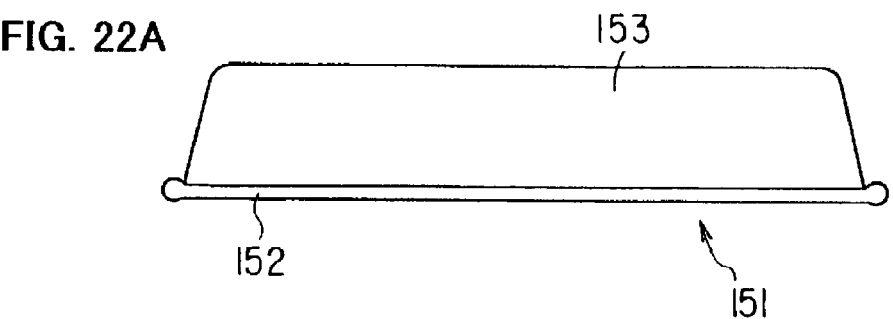
FIG. 22A
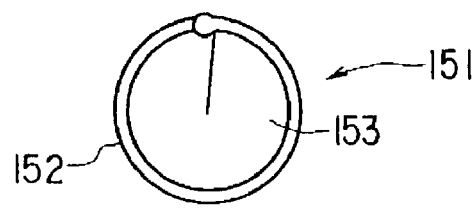
FIG. 22B
FIG. 23
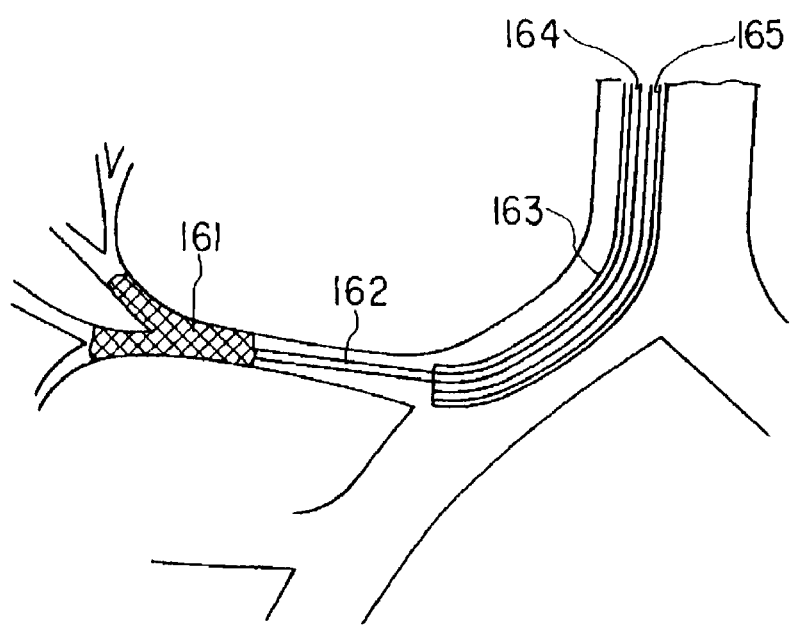

MEDICAL EMBOLIZATION ELEMENT AND METHOD OF EMBOLIZING TUBULAR ORGAN

CROSS-REFERENCE TO RELATED APPLICATION

This application is based upon and claims the benefit of priority from the prior Japanese Patent Application No. 2001-220005, filed Jul. 19, 2001, the entire contents of the application are incorporated herein by reference.

BACKGROUND OF THE INVENTION

1. Field of the Invention

The invention relates to a medical embolization element which is used in an internal cavity of a tubular organ of a subject, and more specifically, to a medical embolization element which is used for embolizing a bronchus, for example, during treatment of lung emphysema.

2. Description of the Related Art

In general, lung emphysema is a morbid change, which is mainly formed by inhalation of harmful substances due to smoking or the like and mainly features wide destruction in peripheral airways and alveoli. The formation of such morbid change is chronic and progressive, and the respiratory function of a patient whose lung emphysema is in an advanced stage is disordered to a remarkable extent. As the basic elements of disfunction of respiratory disorder due to lung emphysema, there are a reduction in resiliency due to destruction of alveoli and a decrease in the area of a functional alveolar membrane. A plurality of elements of disfunction are combined with these basic elements of disfunction to cause a reduction in ventilation efficiency and a decrease in potential ability of breathing, resulting in respiratory disorder.

The lung tissue of a part affected by lung emphysema suffers overexpansion, and cannot achieve sufficient deflation accompanied by expiration. As the volume occupied by the affected part in a pleural cavity becomes larger, a diaphragm and a chest shift to their inflated positions and the driving force of respiratory movement decreases. The remaining normal lung tissue becomes unable to inflate sufficiently in the pleural cavity, and lowers in ventilation efficiency to a remarkable extent.

Primary methods for treatment of lung emphysema is to give a patient bronchodilators, anti-inflammatory agents and antibiotics for treatment of infectious diseases which may occur as complications, and to apply oxygen inhalation to a patient if the patient's affected part is in an advanced stage. Although there may be some cases where the symptoms of the patient are relieved by such internal medicine treatment, the advance of the patient's morbid state cannot be stopped.

On the other hand, surgical treatment can be given to a lung emphysema patient, such as lung volume reduction surgery and lung transplantation. The lung volume reduction surgery surgically removes a part affected by emphysema to recover the remaining normal pulmonary function. In this manner, it is possible to improve the quality of life of the patient, but it is generally necessary to remove a portion as large as about 30% of the lung of the patient. Since this removal imposes a large burden on the patient, it takes a long time for the patient to recover after the surgical operation.

In the case where lung-emphysema-affected parts and normal lung tissues exist in disorder, it is difficult to separate only morbid tissues, so that there is a case in which even normal lung tissues must be removed. In addition, there is also a case where the shape of a serosa, which contains a pulmonary external surface varies, hinders the inflation of the remaining portion of the lung. As a result, there is a case where the function of the remaining normal lung tissue of the patient cannot be fully retained. In addition, since the line of a removed part differs from a natural state and is exposed to nonuniform pressure, there is a case where the tissue of the removed part is broken and pneumothorax occurs. Since lung emphysema is a progressive disease, the remaining portion of the lung of the patient is affected before long. However, the removal of lung tissue imposes a large burden on the body of the patient and, therefore, is difficult to practice repeatedly.

On the other hand, lung transplantation is the only method that can completely cure lung emphysema by replacing a lung of a patient with a normal lung. However, lung transplantation imposes a very large burden on the body of the patient, and entails problems peculiar to transplantation treatment such as immunological problems and the necessity of securing donors. Neither lung volume reduction surgery nor lung transplantation can be easily practiced, because of the problem of requiring a large surgical operation and hence a huge cost for treatment.

Lung volume reduction surgery and lung transplantation, which are practiced as surgical treatment of lung emphysema, have the following problems:

(1) Since lung volume reduction surgery and lung transplantation need a large surgical operation, a large scar is left on the body of a patient.

(2) Neither lung volume reduction surgery nor lung transplantation can be repeatedly practiced on the same patient.

(3) Lung volume reduction surgery cannot be practiced, if an affected part does not exist at a position where it can be easily removed.

(4) There is a case where lung volume reduction surgery cannot fully ensure the function of the remaining portion of the lung.

(5) Both lung volume reduction surgery and lung transplantation require huge costs.

(6) Pnuemothorax may occur after a surgical operation.

(7) There are large obstacles to be surmounted, such as the necessity of securing donors and a rejection of a transplanted piece.

On the other hand, in PCT WO98/48706, an embolization element which gives treatment to lung emphysema by embolizing a bronchus distributed in a lung-emphysema-affected part is described as a device for solving the above-described problems of surgical treatment of lung emphysema. This embolization element is constructed to prevent new air from flowing into the lung-emphysema-affected part, and the air already stored in the lung-emphysema-affected part is carried by blood or the like and naturally decreases. Consequently, the volume of the lung-emphysema-affected part inflated by air decreases, with the result that it is possible to obtain an advantage similar to lung volume reduction surgery. This embolization element has a construction in which a locking element to be locked by being hooked on a living tissue is provided on a peripheral portion of the body of the embolization element. When the embolization element is to be placed in the body, the locking element provided on the periphery of the body of the embolization element is locked by being hooked on the living tissue, so that the embolization element is placed at a desired position in the body.

The embolization element of PCT WO98/48706 has a construction in which a complicated locking element is provided on the peripheral portion of the body of the embolization element in order to place the embolization element at a desired position in the body. However, PCT WO98/48706 has the problem that since the embolization element for giving treatment to lung emphysema is extremely small in size, the work of providing the complicated locking element on the embolization element is difficult.

The present invention has been made, at least in part, by noting the above-described problems, and an object of the invention is to provide a medical embolization element which is used in an internal cavity of a tubular organ of a subject and does not need a complicated locking element, as well as a method of embolizing a tubular organ.

BRIEF SUMMARY OF THE INVENTION

A first aspect of the invention is to make it easy to place a medical embolization element by placing a medical embolization element in a bifurcation of a tubular organ. Specifically, an embolization element is formed in a shape having a plurality of end portions (for example, a stick-like shape, a T shape or a Y shape), and the embolization element is placed in a bifurcation with one of the end portions inserted in one of branch tubular cavities of the bifurcation and the other inserted in the other of the branch tubular cavities. In this manner, the embolization element can be comparatively easily placed in the tubular organ.

At this time, in the case where the embolization element is a stick-like embolization element, it is desirable that the stick-shaped embolization element can be bent according to the relative angle between the two tubular cavities. In addition, even in the case where the embolization element is a T- or Y-shaped embolization element, it is desirable that the angle between its end portions can be changed. One good approach for this construction is to use a resilient substance in (at least a part of) the embolization element. In the case where the resilient substance is used in the embolization element, the embolization element can be locked far more effectively.

It is preferable to prepare an embolization element including a structure having a communication passage formed in its inside, for example, a tubular structure so that a portion which does not need to be embolized can communicate. In addition, it is also preferable to realize embolization by fitting a stop into the communication passage at a later time. According to this construction, it is possible to easily release embolization by removing the stop. In this case, to prevent the stop from easily coming off, it is preferable to provide a projection on the inside wall of the communication passage.

In addition, to prevent the embolization element from easily moving after having been placed, it is preferable to provide a convex part and a concave part on the side surface of a placing object, or to taper the entire side surface of the placing object, or to provide a flange on the side surface.

It is preferable to provide a holding projection on the embolization element so that the embolization element can be easily carried to a placement position.

A second aspect of the invention is that a medical embolization element is locked to a placement position by expanding or extending at the placement position. A first example of this embolization element is an embolization element, which includes a balloon so that the balloon arranged in a reduced state is expanded at a placement position. To expand the balloon, it is preferable to insert a fluid into the balloon through a channel provided in a delivery device such as an endoscope. After expansion, a communication port (through which the fluid flows in) of the balloon may be closed and cut off by the use of a heating element or the like.

A second example of the embolization element is an embolization element in which an element such as sponge having expandability is adopted. It is desirable that the element expands by absorbing moisture. Of course, the element may also be disposed in the balloon.

A third example of the embolization element is an embolization element which includes a wire element such as wire having restoring force and a film attached to the wire element. Until this wire element reaches a placement position, the wire element is deformed so that it can easily pass through a tubular organ, and when reaching the placement position, the wire element restores its original shape by its restoring force. At this time, since the film is provided on the wire element, the embolization element can effectively embolize the placement position.

A third aspect of the invention is an embolization element in which a fluid solidifiable at a placement position is adopted. For example, by discharging such a fluid from the catheter of an endoscope, it is possible to easily embolize a tubular organ.

Examples of a delivery device for carrying each of the embolization elements according to the first, second and third aspects are an endoscope, a catheter extending through a channel of an endoscope, and a dedicated holding element. Each of the embolization elements is carried to a placement position and is released or pushed out at the placement position by any of these delivery devices, and is disconnected from the delivery device and placed in the placement position.

The invention is effective on bronchial embolization, but is not limited to this only. In addition, the term "subject" used herein includes human beings and animals.

BRIEF DESCRIPTION OF THE SEVERAL VIEWS OF THE DRAWINGS

These and other features, aspects, and advantages- of the apparatus and methods of the present invention will become better understood with regard to the following description, appended claims, and accompanying drawings where:

FIG. 4 is a schematic construction view showing the state of distribution of the affected part when a certain period of time passes after the embolization in the use example in which the placing object of the first embodiment is placed in the bifurcation of the bronchial internal cavity.

FIGS. 5A and 5B show a first modification of the placing object of the first embodiment, FIG. 5A being a longitudinal sectional view showing the placing object, and FIG. 5B being a longitudinal sectional view of the essential portions, illustrating the work of inserting the placing object of FIG. 5A into a body by manipulation with a delivery device.

FIGS. 6A is a longitudinal sectional view showing a second modification of the placing object of the first embodiment; FIG. 6B is a longitudinal sectional view showing a third modification of the placing object of the first embodiment; FIG. 6C is a longitudinal sectional view showing a fourth modification of the placing object of the first embodiment; and FIG. 6D is a longitudinal sectional view showing a fifth modification of the placing object of the first embodiment.

FIG. 7 is a longitudinal sectional view showing a sixth modification of the placing object of the first embodiment;

FIG. 8A is a longitudinal sectional view showing a seventh modification of the placing object of the first embodiment; and FIG. 8B is a schematic construction view showing a use example in which the placing object of the seventh modification is placed in a bifurcation of a bronchial internal cavity.

FIGS. 11A to 11D show a third embodiment of the invention, FIG. 11A being a plan view showing the whole of a bronchial embolization device, FIG. 11B being a longitudinal sectional view showing a leading portion of a delivery device, FIG. 11C being a front view of the whole of the bronchial embolization device, showing a state in which a placing object is to be placed, and FIG. 11D being a longitudinal sectional view of the leading portion of the delivery device in the state shown in FIG. 11C.

FIGS. 16A and 16B show a device for retrieving the placing object having the balloon, which is placed in a bronchus, FIG. 16A being a longitudinal sectional view of the essential portions, showing the state in which a leading portion of the retrieving device is located close to the placing object, and FIG. 16B being a longitudinal sectional view of the essential portions showing a state in which the placing object is being retrieved by the retrieving device.

FIG. 17 is a schematic construction view of the whole of a delivery device for a placing object according to a fourth embodiment of the invention.

FIG. 20 is a schematic construction view showing the state in which the placing object of the sixth embodiment is inserted in the internal cavity of a target bronchus by a bronchoscope.

FIGS. 21A and 21B show a seventh embodiment of the invention, FIG. 21A being a perspective view of the essential portions, showing the state in which a sheath and a placing object are attached to a leading portion of an endoscope, and FIG. 21B being a perspective view of the essential portions, showing the state in which the placing object in a placing object accommodation portion is pushed out toward the leading end of the endoscope.

FIGS. 22A and 22B show an eighth embodiment of the invention, FIG. 22A being a plan view showing the state in which a placing object is in a first linear shape, and FIG. 22B being a plan view showing the state in which the placing object is in a second ring- or coil-like shape.

FIG. 23 is a schematic construction view showing the state in which the internal cavity of a bronchus is being embolized by the use of a placing object in a medical embolization element according to a ninth embodiment of the invention.

DETAILED DESCRIPTION OF THE INVENTION

Preferred embodiments of the invention will be described hereinafter with reference to the drawings.

Figure 1A:
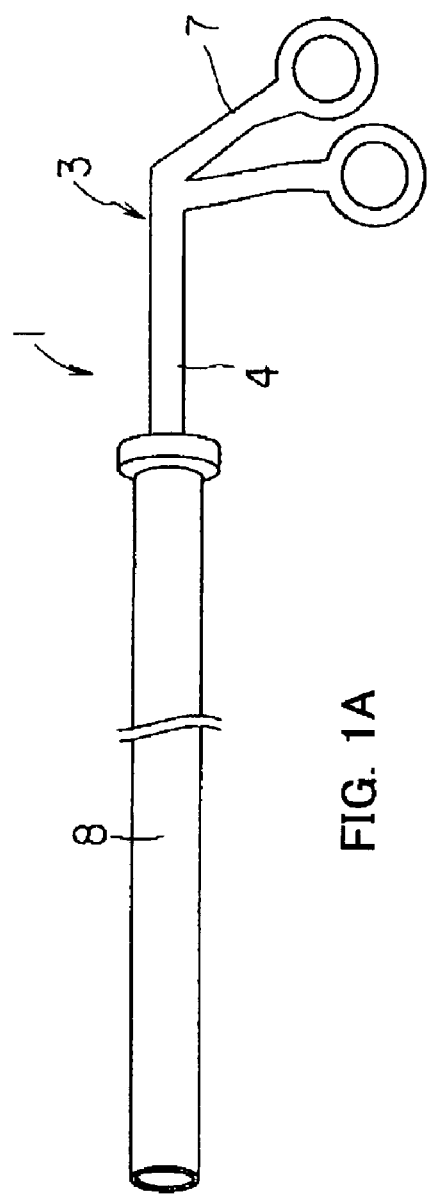
FIGS. 1A to 1C show a first embodiment of the invention, FIG. 1A being a perspective view showing a bronchial embolization device, FIG. 1B being a longitudinal sectional view of the bronchial embolization device, and FIG. 1C being a side view showing a placing object.
Figure 1B:
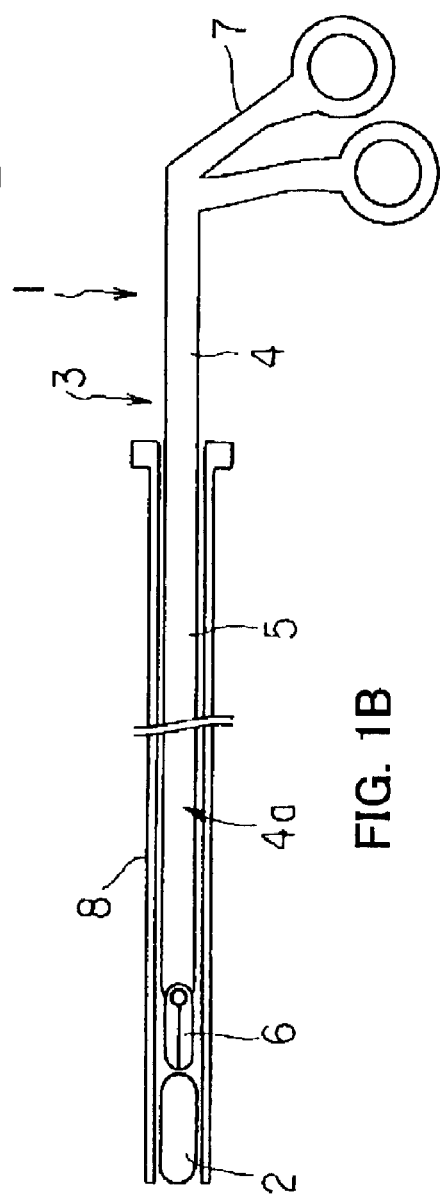

A first embodiment of the invention will be described below with reference to FIGS. 1A to 1C and FIG. 4. In the following description of the first embodiment, reference will be made to a case where a bronchus or a bronchiole, which is a tubular organ, is embolized to give treatment to lung emphysema. Incidentally, the embolization of a bronchus or a bronchiole can be utilized for the treatment of pneumothorax, lung tuberculosis and bronchus tuberculosis. FIGS. 1A to 1B show a bronchus embolization device 1 to be used for embolizing a bronchus in the body of a patient. This bronchus embolization device 1 includes a placing object (placing resilient body) 2, which is a medical embolization element of the first embodiment, and a delivery device 3 for inserting this placing object 2 into the body.

The delivery device 3 is provided with a holding element 4, which holds the placing object 2. This holding element 4 has a holding portion 6, such as a grasper having movable jaws, disposed at a leading portion of an elongated shaft 5. The shaft 5 is made of a flexible or hard material. In addition, a handle 7 for manipulating the holding portion 6 is provided at a proximal portion of the shaft 5. This holding element 4 has an inserting portion 4a in the leading end side of the shaft 5, which inserting portion 4a is to be inserted into the body together with the holding portion 6. Incidentally, it is desirable to minimize stimuli to an airway of the patient by fitting a sheath 8 having smooth surfaces onto the peripheral surface of the inserting portion 4a of the holding element 4.

Figure 1C:
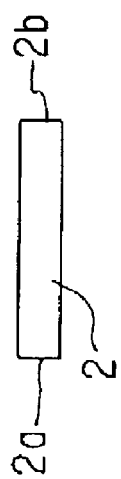
Figure 3:
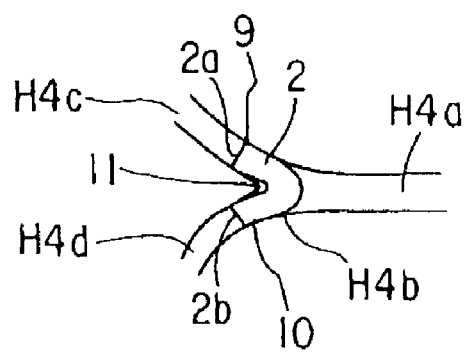
FIG. 3 is a schematic construction view showing the embolized state of a local portion, which state is a use example of the placing object of the first embodiment.

As shown in FIG. 1C, a placing object 2 of the first embodiment is a stick-shaped element which does not have an internal cavity and is made of a soft material having biocompatibility which does not stimulate the mucosa of the airway. Examples of the soft material that can be bent into the position as shown in FIG. 3 include silicon rubber, fluoro rubber and Polyurethane elastomer. Incidentally, both ends 2a and 2b of the placing object 2 may also have curved shapes, which are rounded to minimize stimuli to the airway.

Figure 2:
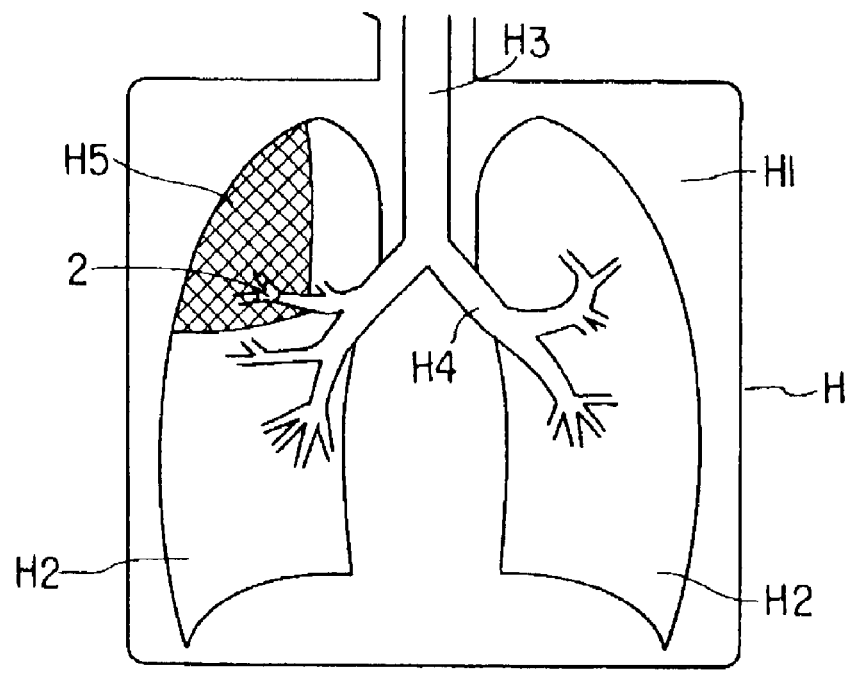
FIG. 2 is a schematic construction view showing the state of distribution of an affected part immediately after embolization in a use example in which the placing object of the first embodiment is placed in a bifurcation of a bronchial internal cavity.

The operation of the above-described construction will be described below. The placing object 2 of the first embodiment is inserted into the body of a patient H as shown in FIG. 2, by the delivery device 3 shown in FIGS. 1A and 1B. In FIG. 2, symbol H1 denotes a pleural cavity, symbol H2 denotes a lung, symbol H3 denotes a trachea, symbol H4 denotes a bronchus, and symbol H5 denotes a lung-emphysema-affected part. The placing object 2 of the first embodiment is inserted into the internal cavity of the bronchus H4, which is distributed in the lung-emphysema-affected part H5, in the state of being held by the holding element 4 of the delivery device 3. The placing object 2 inserted into the internal cavity of the bronchus H4 is inserted from a central-side bronchus H4a toward a bifurcation H4b of the bronchus H4, as shown in FIG. 3. The guidance of the placing object 2 toward a placement position is performed with an X-ray radioscopy or an endoscope.

Moreover, the placing object 2 of the first embodiment which has been inserted into the internal cavity of the bronchus H4 is bent in its middle portion into an approximately V shape. The end 2a of the placing object 2 is inserted from the bifurcation H4b of the bronchus H4 into a first branch tubular cavity H4c which is one bronchus H4c of two peripheral-side bronchi H4c and H4d, thereby forming a first embolization portion 9 capable of sealing the first branch tubular cavity H4c. The other end 2b of the placing object 2 is inserted into a second branch tubular cavity H4d, which is the other bronchus H4d, thereby forming a second embolization portion 10 capable of sealing the second branch tubular cavity H4d.

Furthermore, a locking portion 11 capable of being locked to an edge portion of the junction portion between the first and second branch tubular cavities H4c and H4d at the bifurcation H4b of the bronchus H4 is formed in the V-shaped bent portion between the first embolization portion 9 and the second embolization portion 10 of the placing object 2. The two bronchi H4c and H4d lying on the peripheral side of the bifurcation H4b of the bronchus H4 and the bronchus H4a lying on the central side of the bifurcation H4b, i.e., three portions, are embolized by the placing object 2 of the first embodiment, as shown in FIG. 3, whereby the internal cavity of the target bronchus H4 is completely embolized. Incidentally, the placing object 2 of the first embodiment may also be placed by using forceps of a bronchoscope or the like instead of the delivery device 3 shown in FIGS. 1A and 1B.

Treatment of lung emphysema according to the invention will be described below with reference to FIGS. 2 and 4 which are schematic views showing the pleural cavity H1 of a human being. FIG. 2 shows a state in which the internal cavity of the bronchus H4 distributed in the lung-emphysema-affected part H5 is embolized by the placing object 2. As shown in FIG. 2, at a time immediately after the placing object 2 embolized, the lung-emphysema-affected part H5 occupies a large volume of the pleural cavity H1 of the patient, but the air stored in the lung-emphysema-affected part H5 is absorbed with time, and the volume of the lung-emphysema-affected part H5 decreases as shown in FIG. 4. Accordingly, the healthy portion of the lung H2 of the patient that is decreased in ventilation function by being suppressed by the lung-emphysema-affected part H5 can be expanded to relieve the ventilation function, whereby the quality of life of the patient is improved.

The above-described construction has the following advantages. When the placing object 2 of the first embodiment is in use, the first branch tubular cavity H4c of the bifurcation from which a tubular cavity branches off into a plurality of tubular cavities in the internal cavity of the bronchus H4 distributed in the lung-emphysema-affected part H5 is sealed by the first embolization portion 9, while the second branch tubular cavity H4d which is the other of the bifurcation portions is embolized by the second embolization portion 10, and in this state, the locking portion 11 is locked to the edge portion of the junction portion between the first and second branch tubular cavities H4c and H4d, whereby the placing object 2 is placed in the bifurcation H4b. Accordingly, the internal cavity of the bronchus H4 distributed in the lung-emphysema-affected part H5 can be completely embolized by the placing object 2 to prevent new air from flowing into the lung-emphysema-affected part H5. The volume of the lung-emphysema-affected part H5 before treatment is very large because excess air is stored in the lung-emphysema-affected part H5, but since this air has been carried to the affected portion via the bronchus H4 of the lung-emphysema-affected part H5, the stored air is carried by a blood flow or the like and naturally decreases, by intercepting the supply of air to the lung-emphysema-affected part H5. Consequently, the volume of the lung-emphysema-affected part H5 expanded by air decreases, so that it is possible to achieve an advantage similar to the lung volume reduction surgery. Accordingly, it is possible to give treatment to lung emphysema without a large invasion into the body of the patient, unlike related-art surgical treatment of lung emphysema.

In addition, in the first embodiment, the placing object 2 and the delivery device 3 have simple constructions and low cost. Moreover, the first embodiment has the advantage that it is possible to repeatedly give treatment to lung emphysema with the placing object 2 of the first embodiment.

Incidentally, the first embodiment may also have a construction which serves a movement-preventing action to make it difficult for the placing object 2 to move in the internal cavity of the bronchus H4, by increasing the length of the stick-shaped placing object 2 of the first embodiment and increasing the area of the placing object 2 which comes into contact with the wall of the bronchus H4. The placing object 2 of the first embodiment may also be held and retrieved by, for example, a device similar to the delivery device 3.

FIGS. 5A and 5B show a first modification of the placing object 2 of the first embodiment. The first modification has a construction in which a projection 21 for facilitating manipulation by the holding element 4 of the delivery device 3 is provided on the peripheral surface of the stick-shaped placing object 2 of the first embodiment. The position of the projection 21 may be anywhere on the external surface of the placing object 2.

When the placing object 2 of the first modification is to be inserted into the body by the manipulation of the holding element 4 of the delivery device 3, the projection 21 of the placing object 2 can be held by the holding portion 6 at a leading portion of the holding element 4 as shown in FIG. 5B. Accordingly, the manipulation of holding the placing object 2 by the holding element 4 can be facilitated. To accommodate the placing object 2 in the sheath 8 before the insertion, the operator projects the holding portion 6 from the tip of the sheath 8, opens the jaws of the holding portion 6 and holds the projection 21 of the placing object 2 by the jaws. And the operator bends the placing object 21 by his fingers and retracts the holding portion 6 and placing object 2 into the leading portion of the sheath 8.

The stick-shaped placing object 2 of the first embodiment may have other constructions such as modifications shown in FIGS. 6A to 6D, respectively. FIG. 6A shows a second modification of the first embodiment. The second modification has a construction in which a notch 22 for facilitating bending of the placing object 2 is provided at at least one location of the placing object 2. The notch 22 corresponds to junction 11 when the placing object 2 is placed.

FIG. 6B shows a third modification of the placing object 2 of the first embodiment. The third modification has a construction in which flange-shaped stopper portions 23a and 23b for preventing the vibration of the placing object 2 in an airway are provided at both ends 2a and 2b of the placing object 2, respectively. Incidentally, markers 24 which are X-ray-impermeable marks may also be provided on the placing object, such as on the stopper portions 23a and 23b, respectively.

FIG. 6C shows a fourth modification of the placing object 2 of the first embodiment. The fourth modification has a construction having an external surface having an undulated portion, such as a plurality of large-diameter convex parts 25 juxtaposed on the peripheral surface of the placing object 2 along a length thereof, where the diameter of the placing object 2 continuously changes between concave parts 26 between the front and rear convex parts 25. The distance between the front and rear convex parts 25 is set to approximately 3 mm to 10 mm, for example, to correspond to the concave and convex parts of the internal cavity of the bronchus H4.

FIG. 6D shows a fifth modification of the placing object 2 of the first embodiment. The fifth modification has a construction in which a taper 27 having the shape of an approximately conic cylinder is formed on the peripheral surface of the placing object 2 and the diameter of the placing object 2 is continuously changed. Incidentally, the delivery device 3 is replaced according to the shape of the placing object 2.

FIG. 7 shows a sixth modification of the placing object 2 of the first embodiment. The sixth modification is provided with a placing object 31 made of a soft material formed in a tubular shape as a whole. Examples of the soft material include those discussed above with regard to placing object 2. The tubular placing object 31 can be inserted in the way of being fitted on a leading portion of the delivery device 3.

The tubular placing object 31 may have the shape of a tube which is closed at one of the opposite ends 31a and 31b, in addition to the shape of a simple tube which are opened at the opposite ends 31a and 31b as shown in FIG. 7. By changing combinations of these open and closed ends of the tube, it is possible to change portions to be embolized; for example, only one of the peripheral-side bronchi H4c and H4d may be embolized or both of the peripheral-side bronchi H4c and H4d may be embolized.

FIGS. 8A and 8B show a seventh modification of the placing object 2 of the first embodiment. The seventh modification has a construction in which, as shown in FIG. 8A, the tubular placing object 31 has a closed end portion 32 at the one end 31a and an open end portion 33 at the other end 31b. Moreover, in the seventh modification, a circular hole 34 is formed in the placing object 31 in the middle portion of the peripheral surface thereof.

When the placing object 31 of the seventh modification is in use, as shown in FIG. 8B, for example, the closed end portion 32 at the one end 31a of the placing object 31 is inserted into the first branch tubular cavity H4c which is one of the peripheral-side bronchi, to seal the first branch tubular cavity H4c. After that, the leading portion of the delivery device 3 is inserted into the circular hole 34 in the middle portion of the placing object 31, whereby the open end portion 33, which is the other open end portion of the placing object 31, can be introduced into the internal cavity of the second branch tubular cavity H4d which is the other of the peripheral-side bronchi. In the example of use in which the placing object 31 of the seventh modification is placed in the bifurcation of the internal cavity of the bronchus H4 as shown in FIG. 8B, the first branch tubular cavity H4c which is one of the peripheral-side bronchi is embolized, while the second branch tubular cavity H4d which is the other of the peripheral-side bronchi can be held in an open state.

Accordingly, in the case of the tubular placing object 31 of the seventh modification, by changing combinations of the closed end portion 32, the open end portion 33 and the circular hole 34, it is possible to arbitrarily change the state of embolization of the internal cavity of the bronchus H4 by the placing object 31. Incidentally, the tubular placing object 31 may also have a construction in which a notch extending in its longitudinal direction is provided in the peripheral surface.

Figure 9A:
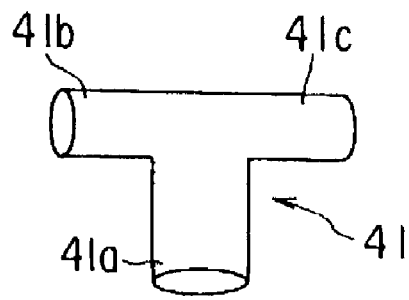
FIGS. 9A to 9C show a second embodiment of the invention, FIG. 9A being a perspective view showing a T-shaped placing object, FIG. 9B being a front view showing a Y-shaped placing object, and FIG. 9C being a schematic construction view showing a use example in which the placing object is placed in a bifurcation of a bronchial internal cavity.
Figure 9B:
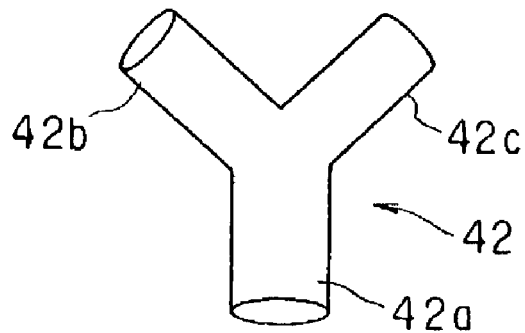
Figure 9C:
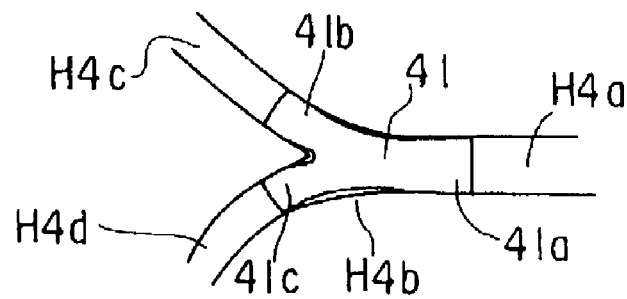

FIGS. 9A to 9C show a second embodiment of the invention. The second embodiment has a construction in which a placing object 41 having a T shape as shown in FIG. 9A or a placing object 42 having a Y shape as shown in FIG. 9B is provided instead of the stick-shaped placing object 2 of the first embodiment (refer to FIGS. 1A to 1C and 4). Examples of the material of placing objects 41 and 42 include silicon rubber, fluoro rubber and Polyurethane elastomer. As shown in FIG. 9A, the T-shaped placing object 41 is made of one central tube 41a to be positioned on the central side during use, and two peripheral tubes 41b and 41c to be positioned on the peripheral side during use.

In addition, as similarly shown in FIG. 9B, the Y-shaped placing object 42 is made of one central tube 42a to be positioned on the central side during use, and two peripheral tubes 42b and 42c to be positioned on the peripheral side during use.

When either of the placing objects 41 or 42 of the second embodiment is in use, at least one of the internal cavities of the central tube 41a or 42a and the peripheral tubes 41b and 41c or 42b and 42c is completely embolized (closed) in order to embolize the two bronchi H4c and H4d lying on the peripheral side of the bifurcation H4b of the bronchus H4.

Incidentally, the diameter of each of the central tubes 41a and 42b and the peripheral tubes 41b, 41c, 42b and 42c is desirably made coincident with the internal diameter of a bronchus of a placement part.

The operation of the second embodiment having the above-described construction will be described below. FIG. 9C shows the state in which the placing object 41 of the second embodiment is placed in the internal cavity of the bronchus H4 of the bronchus bifurcation H4b distributed in an affected part. In FIG. 9C, the central tube 41a is inserted in the internal cavity of the bronchus H4a lying on the central side of the bronchus bifurcation H4b, while the peripheral tubes 41b and 41c are respectively inserted in the internal cavities of the two bronchi H4c and H4d lying on the peripheral side of the bronchus bifurcation H4b. In this state, since the peripheral tubes 41b and 41c spread in branches from the bronchus bifurcation H4b toward the peripheral side, the peripheral tubes 41b and 41c prevent the vibration of the placing object 41 in the internal cavity of the bronchus H4.

In addition, since at least one of the peripheral tubes 41b and 41c of the placing object 41 has completely closed end, at least one of the internal cavities of the two bronchi H4c and H4d lying on the peripheral side of the bronchus bifurcation H4b, in which the placing object 41 is placed, is completely embolized. Incidentally, in the case where all portions of the placing object 41 are hollow, at least one of the peripheral tubes 41b and 41c or the central tube 41a is completely embolized with a stop or the like after the placing object 41 is placed.

Accordingly, in the second embodiment, by placing the T-shaped placing object 41 or the Y-shaped placing object 42 in the bifurcation H4b of the bronchus H4, it is possible to embolize the two bronchi H4c and H4d lying on the peripheral side if at least one of the peripheral tubes 41b, 41c or the central tube 41a is closed. Therefore, similarly to the case of the first embodiment, it is possible to completely embolize the internal cavity of the bronchus H4 distributed in the lung-emphysema-affected part H5 by means of the T-shaped placing object 41 or the Y-shaped placing object 42. Accordingly, it is possible to achieve an advantage similar to that of the first embodiment.

In the second embodiment in particular, the T-shaped placing object 41 or the Y-shaped placing object 42 which is close in shape to the bifurcation H4b of the bronchus H4 is provided, so that the second embodiment has the advantage that stimuli to the mucosa of the bronchus is small irrespective of the material of the placing object. Moreover, the second embodiment has the advantage of reliably fixing the placing object to a bronchus.

Figure 10A:
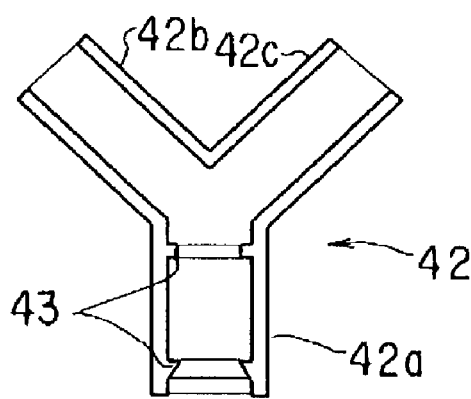
FIG. 10A is a longitudinal sectional view showing a first modification of the Y-shaped placing object of the second embodiment.

FIG. 10A shows a first modification of the Y-shaped placing object 42 of the second embodiment. The first modification is provided with an embolization element 44 which plugs up the central tube 42a of the placing object 42. As shown in FIG. 10A, embolization element locking claws 43 are formed to project inward from the internal surface of the central tube 42a of the placing object 42.

In addition, the embolization element 44 is a non-void element which is made of a resilient material and has approximately the same shape as the internal cavity of the central tube 42a. The outside diameter of the embolization element 44 is set to be approximately the same as the inside diameter of the central tube 42a. Furthermore, a projection 45 for facilitating manipulation by the delivery device 3, by a holding portion 6 or other grasping device, is provided on the peripheral surface of the embolization element 44.

In the second embodiment, in the case where the central tube 42a of the placing object 42 is not embolized, the embolization element 44 can be inserted into the internal cavity of the central tube 42a by the delivery device 3 to plug up the central tube 42a of the placing object 42. In the case where the embolization element 44 is inserted into the interior of the placing object 42, the embolization element locking claws 43 lock to the end edge portions of the embolization element 44 to reliably fix the embolization element 44 to the internal cavity of the central tube 42a.

Figure 10B:
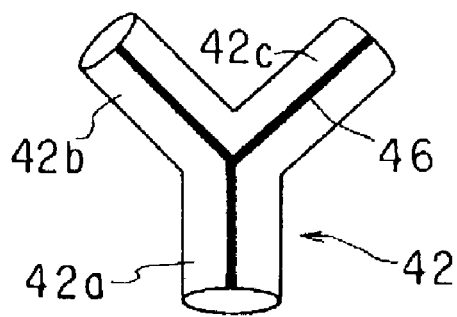
FIG. 10B is a perspective view showing a second modification of the Y-shaped placing object of the second embodiment.

As in a second modification of the Y-shaped placing object 42 of the second embodiment shown in FIG. 10B, an X-rays-impermeable marker 46 made of an X-rays-impermeable material such as metal wire may also be provided on the peripheral surface of the placing object 42.

Incidentally, each of the placing object 2 of the first embodiment (refer to FIGS. 1A to 1C) and the T- and Y-shaped placing objects 41 and 42 of the second embodiment (refer to FIGS. 9A to 9C) may have a projection or a hole, similar to the projection 45, which assists in manipulation by the delivery device 3 when the placing objects 2, 41 and 42 are used in combination with the delivery device 3. The placing objects 2, 41 and 42 temporarily placed by the use of the projection or hole may also be constructed to be retrievable.

Moreover, in the case where each of the placing object 2 of the first embodiment and the T- and Y-shaped placing objects 41 and 42 of the second embodiment has a hollow shape closed at one end, the material of the closing surface may be a transparent material, such as polyethylene or polypropylene. In this case, when any of the placing object 2 of the first embodiment, the T-shaped placing object 41 of the second embodiment and the Y-shaped placing object 42 of the second embodiment is fitted on the tip of an endoscope and manipulated for placement, the view of the endoscope can be secured through the transparent material. Furthermore, an X-rays-impermeable marker which is a mark impermeable to X rays may be provided on not only the placing object but also the delivery device 3 as position identification means to be used during and after treatment.

FIGS. 11A to 11D show a third embodiment of the invention. FIG. 11A shows a bronchial embolization device 51. As shown in FIG. 11B, this embolization device 51 includes a placing object 52 which is a medical embolization element of the third embodiment, and a delivery device 53 for inserting this placing object 52 into the body of a patient.

The delivery device 53 is provided with an elongated inserting portion 54 to be inserted into the body, and an operator-side manipulation portion 55, which is connected to a proximal portion of this inserting portion 54. The inserting portion 54 is provided with an elongated sheath tube 56. A placing object accommodation portion 57 into which to accommodate the placing object 52 is provided in a leading portion of the sheath tube 56. Furthermore, an elongated wire-like push-out element 58 is inserted for sliding movement forward and rearward in the interior of the sheath tube 56 behind the placing object accommodation portion 57.

The manipulation part 55 is provided with an elongated manipulation part body 59 having an approximately tubular shape. The manipulation part body 59 has a slot-shaped guide groove 60 formed to extend along its axis. The manipulation part 55 also has a manipulation knob 61 of the push-out element 58 disposed for movement along the guide groove 60. A proximal portion of the push-out element 58 is connected to the manipulation knob 61. When the manipulation knob 61 is made to move forward or rearward, the push-out element 58 moves with respect to the sheath tube 56 along the axis thereof.

When the manipulation knob 61 is in the state of being moved to the position of a proximal portion (in FIG. 11A, the right-hand end) of the guide groove 60 of the manipulation part body 59 as shown in FIG. 11A, a leading portion of the push-out element 58 is withdrawn into the interior of the sheath tube 56 as shown in FIG. 11B. In the interior of the sheath tube 56, the placing object accommodation portion 57 is formed in a portion immediately before the leading portion of the push-out element 58 so that the placing object 52 can be accommodated in the placing object accommodation portion 57.

When the manipulation knob 61 is moved to the position of a leading portion (in FIG. 11C, the left-hand end portion) of the guide groove 60 of the manipulation part body 59 as shown in FIG. 1C, the leading portion of the push-out element 58 enters the placing object accommodation portion 57 and the placing object 52 is pushed out to the leading end position of the sheath tube 56, as shown in FIG. 1D. Thus, the push-out element 58 pushes out the placing object 52 from the interior of the placing object accommodation portion 57.

The placing object 52 has a construction capable of assuming two shapes, one of which is a small-volume shape that the placing object 52 assumes when it is accommodated in the placing object accommodation portion 57 of the delivery device 53, and the other of which is a large-volume shape that the placing object 52 assumes when it is placed in a target part. The placing object 52 is made of, for example, sponge having a very large expandability showing an expansion coefficient of ten times or more in terms of volume ratio. This placing object 52 can be inserted in a compressed shape into the placing object accommodation portion 57 of the delivery device 53.

Incidentally, the sponge-like placing object 52 may also have a construction that does not need external force nor an accommodating tool to maintain the compressed shape. An example of the placing object 52 having such a construction is a placing object made of a material (for example, cellulose) which enables the compressed shape to be maintained in the air and can be very greatly expanded by absorbing moisture.

By manipulating the bronchial embolization device 51 of the third embodiment in a manner similar to that performed in the first embodiment, the sponge-like placing object 52 is placed into the bifurcation H4b of the bronchus H4 to embolize three portions, i.e., the two bronchi H4c and H4d lying on the peripheral side of the bifurcation H4b of the bronchus H4 and the bronchus H4a lying on the central side of the bifurcation H4b, whereby the internal cavity of the target bronchus H4 can be completely embolized. Accordingly, it is possible to achieve an advantage similar to that of the first embodiment.

Moreover, the third embodiment is provided with the sponge-like placing object 52 which can assume two shapes, i.e., the small-volume shape that the placing object 52 assumes when it is accommodated in the placing object accommodation portion 57 of the delivery device 53, and the large-volume shape that the placing object 52 assumes when it is placed in an target part, whereby the placing object 52, although it has one shape, can be applied to a wide range of bronchial diameters of bronchi in which to place the placing object 52.

Figure 12A:
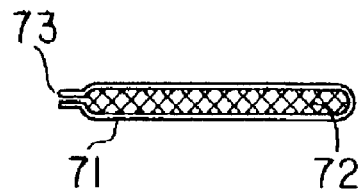
FIGS. 12A and 12B show a modification of the placing object of the third embodiment, FIG. 12A being a longitudinal sectional view showing a reduced state of a balloon in which the placing object is accommodated, and FIG. 12B being a longitudinal sectional view showing an expanded state of the balloon in which the placing object is accommodated.
Figure 12B:
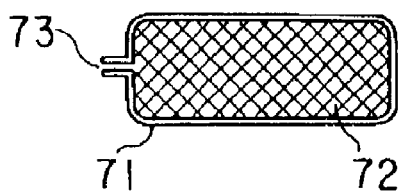

FIGS. 12A and 12B show a modification of the placing object 52 of the third embodiment (refer to FIGS. 11A to 11D). According to this modification, a placing object 72 made of an expansive material such as sponge is contained in a balloon 71. At least a part of this balloon 71 has a communication port 73 for communication with the outside space.

The peripheral surface of the placing object 72 of this modification is covered with the balloon 71. When the placing object 72 is in the state of being accommodated in the placing object accommodation portion 57 of the delivery device 53, the expansive material of the placing object 72 contained in the balloon 71 is held in a reduced shape compressed as shown in FIG. 12A. When the placing object 72 is pushed out of the placing object accommodation portion 57 by the push-out element 58 in order that the placing object 72 is placed into the body of a patient, the balloon 71, after the placing object 72 has moved out of the placing object accommodation portion 57, naturally expands by the restoring force of the sponge itself as shown in FIG. 12B and is placed into the internal cavity of a bronchus.

Incidentally, it is desirable that the communication port 73 for the placing object 72 in the balloon 71 have a construction which can be embolized after placement, for example, a construction which can be fused by heat or a construction which can be mechanically embolized by manipulation using forceps or the like.

Figure 13A:
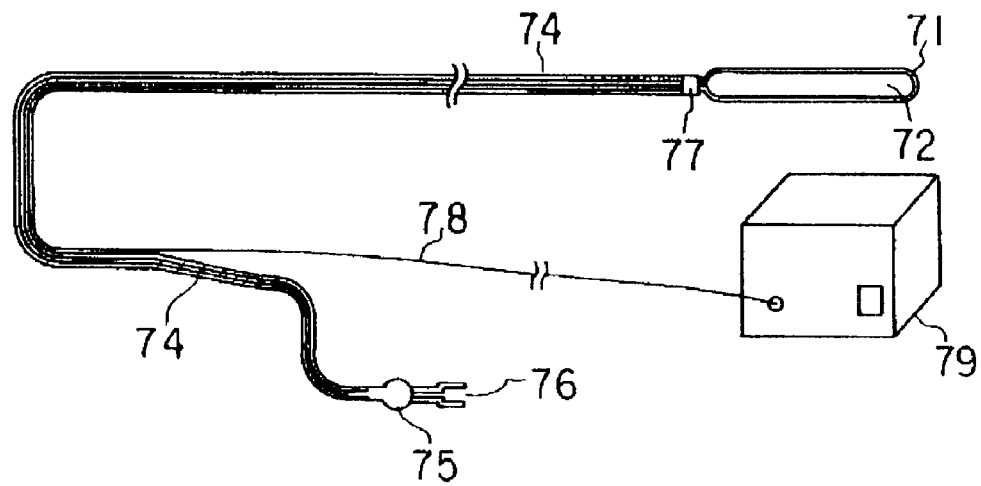
FIG. 13A is a schematic construction view showing the state in which the balloon which contains the placing object in its inside is connected to a catheter.

A delivery device for the placing object 72 having the balloon 71 preferably has a construction which communicates with an operator side through a small-diameter catheter 74 as shown in FIG. 13A. The balloon 71, which has in its interior the expansive material constituting the placing object 72, is connected to a leading portion of the catheter 74. The operator-side end of the catheter 74 is provided with an opening portion 76 and a valve, such as a three-way cock 75, which opens and closes the opening portion 76 and holds airtightness when the opening portion 76 is closed.

Before placement, as shown in FIG. 13A, the air or the like inside the balloon 71 is sucked through the opening portion 76 of the operator-side end of the catheter 74, and the balloon 71 is reduced to a small diameter. After the placing object 72 is inserted into a placement part of the body of a patient, when the three-way cock 75 is manipulated to open the opening portion 76 of the operator-side end of the catheter 74, air enters the balloon 71 through the catheter 74 and the sponge of the placing object 72 in the balloon 71 expands by its restoring force.

Incidentally, not only a gas but a liquid may also be charged into the balloon 71 through the catheter 74. For example, if the expansive material inside the balloon 71 is a material which expands by water, water is injected through the opening portion 76 of the operator-side end of the catheter 74.

A heating element 77 that generates heat by application of electricity is provided near a portion for connection to the balloon 71 at the leading portion of the catheter 74. One end of a coaxial cable 78 is connected to the heating element 77. The other end of the coaxial cable 78 leads to the operator-side end of the catheter 74 along the inside or the outside of the catheter 74, and is connected to a power source box 79.

Figure 13B:
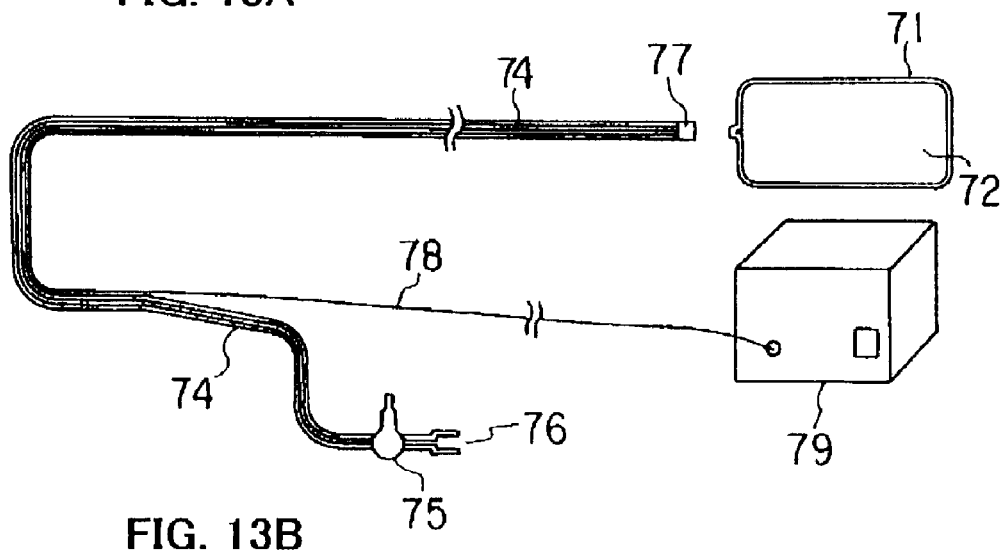
FIG. 13B is a schematic construction view showing a state in which the balloon which contains the placing object in its inside is cut from the catheter.

When electricity is applied to the coaxial cable 78, the balloon 71 which accommodates the placing object 72 is cut from the catheter 74 by heat generated by the heating element 77, as shown in FIG. 13B. At this time, when the catheter 74 is cut, the cut end of the catheter 74 is fused and embolized.

Figure 14A:
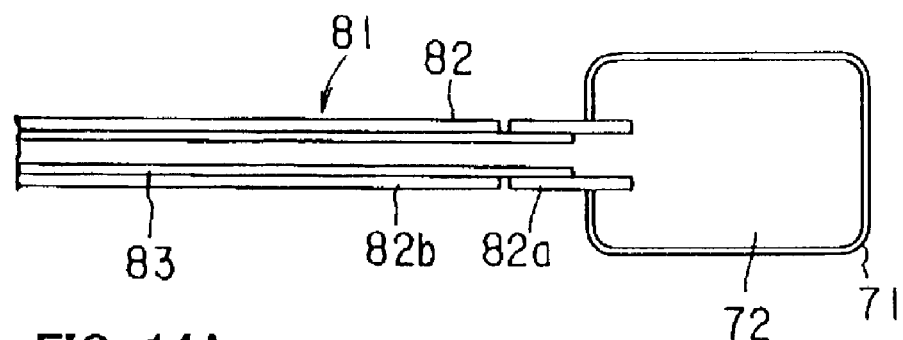
FIGS. 14A and 14B show a device which cuts the balloon from a double catheter by sliding the inner catheter of the double catheter backward, FIG. 14A being a longitudinal sectional view of the essential portions, showing the state in which the balloon is connected to the double catheter, and FIG. 14B being a longitudinal sectional view of the essential portions, showing the state in which the balloon which contains the placing object in its inside is cut from the double catheter.
Figure 14B:
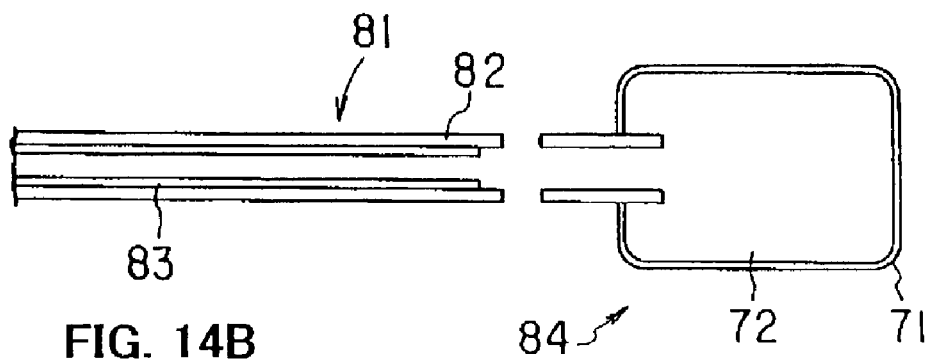

FIGS. 14A and 14B show a modification of a device which cuts the balloon 71 which accommodates the placing object 72, from the catheter 74. This modification uses a catheter 81 having a double tube structure. This catheter 81 having a double tube structure is provided with an outside catheter 82 and an inside catheter 83. As shown in FIG. 14A, each of the outside catheter 82 and the inside catheter 83 is connected to the balloon 71.

Furthermore, the outside catheter 82 is divided into a short distal portion 82a which is connected to the balloon 71, and a long catheter body portion 82b which leads to an operator-side portion. Before placement, as shown in FIG. 14A, a leading portion of the inside catheter 83 is disposed to extend into the distal portion 82a of the outside catheter 82.

At the time of placement, when the inside catheter 83 is slid toward the operator side, as shown in FIG. 14B, a placing unit 84 which is made of the balloon 71 which accommodates the placing object 72 and the distal portion 82a of the outside catheter 82 comes off the catheter body portion 82b of the outside catheter 82 and the inside catheter 83.

In the case where the placing object 72 inside the balloon 71 has a construction which does not need to inject a liquid or the like into the balloon 71 from the opening portion 76 at the operator-side end of the placing object 72, the inside catheter 83 does not need to be hollow.

Figure 15A:
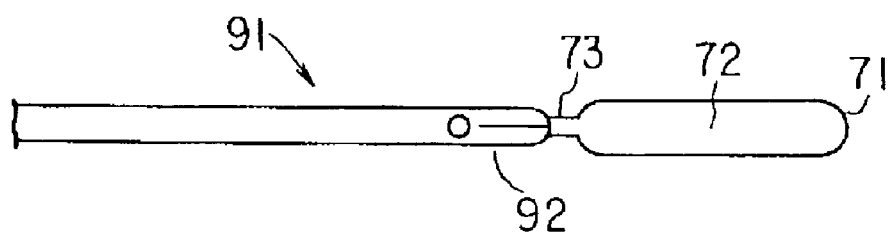
FIGS. 15A and 15B show a device which inserts a balloon by means of a small-diameter holding element which is usable in the state of being inserted in a channel of a bronchoscope, FIG. 15A being a side view of the essential portions, showing the state in which the balloon is held by the holding element, and FIG. 15B being a side view of the essential portions, showing the state in which the balloon is cut from the holding element.
Figure 15B:
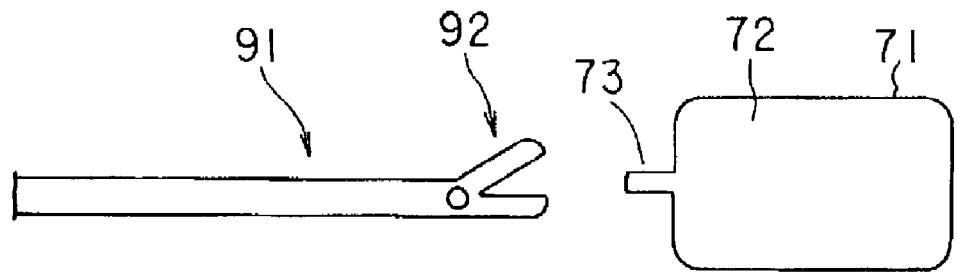

FIGS. 15A and 15B show a device which inserts the balloon 71 by a small-diameter holding element 91 which can be used while being inserted in the channel of a bronchoscope. The placing object 72 is made of a material that has expandability and whose outside is covered with the balloon 71, and a part of the balloon 71 has the communication port 73.

Furthermore, the communication port 73 is disposed at a part which can be held by the holding element 91. Before placement, as shown in FIG. 15A, the balloon 71 and the placing object 72 made of the expansive material inside the balloon 71 are held in a fully compressed state by a holding portion 92 of the holding element 91. During this time, when the balloon 71 and the placing object 72 are in the state held by the holding portion 92 of the holding element 91, the communication port 73 of the balloon 71 is completely closed so that the airtightness of the balloon 71 is held.

When the holding element 91 is disconnected from the balloon 71 as shown in FIG. 15B to place the placing object 72, the communication port 73 of the balloon 71 opens and the expansive material inside the balloon 71 expands, to embolize a bronchus. At this time, a substance, which is needed when the expansive material inside the balloon 71 is to be expanded, is injected into the balloon 71 through the communication port 73.

In addition, when the placing object 72 is to be inserted into the bronchus by the use of the channel of the bronchoscope, the elongated holding element 91 which can pass through the interior of the channel of the bronchoscope is temporarily inserted into the channel of an endoscope, and a leading portion of the holding element 91 is projected from the leading portion of the endoscope so that the holding element 91 can hold the placing object 72.

In this method, since the diameter of the placing object 72 need not be made as small as the placing object 72 can pass through the channel of the endoscope, a large placing object 72 can be inserted, with the result that a large-diameter Bronchus can be embolized.

FIGS. 16A and 16B show a device 101 for retrieving, for example, the placing object 72 having the balloon 71 temporarily placed in a bronchus. This retrieving device 101 is provided with a holding portion 103 for holding the placing object 72 and a sharply pointed hollow needle 104 for puncturing the balloon 71, at a leading portion of a wire-like elongated inserting portion 102. This hollow needle 104 is positioned in the holding portion 103 when the holding portion 103 of the retrieving device 101 is closed, and when the holding portion 103 is opened, the hollow needle 104 is exposed.

A leading portion of the retrieving device 101 is inserted into the channel of a bronchoscope 105 and reaches the placing object 72 placed in the internal cavity of the bronchus H4. Then, as shown in FIG. 16A, the leading portion of the retrieving device 101 is forced against the placing object 72 with the holding portion 103 opened, whereby the point of the hollow needle 104 penetrates into the balloon 71 and reaches the internal cavity of the balloon 71. At this time, the balloon 71 is broken by the hollow needle 104 and the inside and the outside of the balloon 71 are made to communicate with each other, whereby the content of the balloon 71 leaks out. Accordingly, the tension of the balloon 71 is relaxed, so that the balloon 71 can be easily compressed.

After that, as shown in FIG. 16B, the holding portion 103 of the retrieving device 101 is closed to hold and draw the balloon 71, whereby the balloon 71 can be easily drawn out of an airway. In the case where the hollow needle 104 is connected to an operator-side control portion via a tube, after the hollow needle 104 has punctured to hold the balloon 71, the content of the balloon 71 of the placing object 72 is sucked from the operator side of the tube, whereby the placing object 72 can be reduced and easily removed from the airway.

Incidentally, the retrieving device 101 may also include in combination a simple tube-shaped element having a comparatively large diameter and a bronchoscope or a holding element. The embolization device 51 of the third embodiment may also include in combination the balloon 71 in which the placing object 72, the delivery device 53 and the retrieving device 101. In this case, since the retrieval of the placing object 72 is easy, placement positions can be changed or the placing object 72 can be removed after treatment.

FIG. 17 shows a fourth embodiment of the invention. In the fourth embodiment, the construction of the placing object 72 in the balloon 71 shown in FIGS. 13A and 13B is modified as follows. Incidentally, the constructions of the other portions shown in FIG. 17 are the same as those of the corresponding portions of the device shown in FIGS. 13A and 13B, and in FIG. 17, the same reference numerals are used to denote the portions which are the same in construction as those of the device shown in FIGS. 13A and 13B and the description thereof is omitted hereinafter.

In the fourth embodiment, a placing object 111 in the balloon 71 is formed of an injection material which has a first form having fluidity like that of a liquid and a second form having a comparatively small fluidity like that of a gel or a solid. A transition from the first form to the second form of the injection material, which is the placing object 111, is caused by a method such as a method of mixing two liquids having different fluidities. Materials having such properties are, for example, alginic acid which transforms from liquid form to gel form by addition of particular ions, and silicone which transforms from liquid form to solid form by addition of a curing agent.

The catheter 74 connected to the balloon 71 which accommodates the placing object 111 may have a tubular structure made of a simple tube, but may also have a structure having two internal cavities respectively provided with two tubes 74a and 74b through which two different injection materials can be separately injected.

In the fourth embodiment, by injecting a material of low fluidity as the content of the placing object 111 in the balloon 71, it is possible to impart deformation-resistant properties to the balloon 71 of the placing object 111. In addition, by imparting the first form like a liquid form having fluidity to the placing object 111 in the balloon 71, it is possible to make the shape of the placing object 111 coincident with the shape of a bronchus of an embolized part.

Figure 18A:
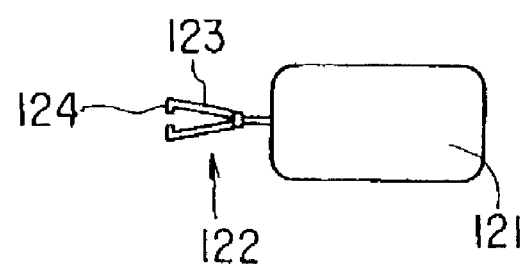
FIGS. 18A and 18B show a fifth embodiment of the invention, FIG. 18A being a side view showing a placing object for a medical embolization element, and FIG. 18B being a schematic construction view showing the state in which the placing object is fixed to the wall of a bronchus from the internal cavity of the bronchus.
Figure 18B:
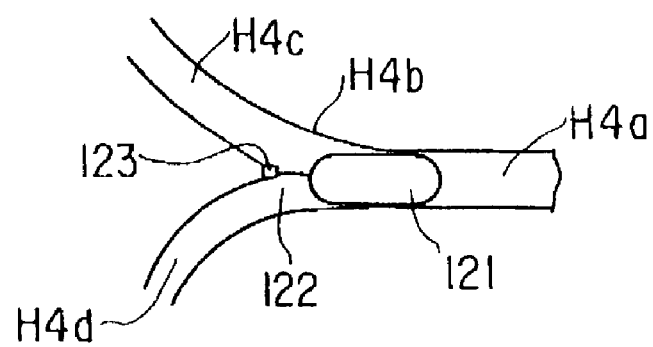

FIGS. 18A and 18B show a fifth embodiment of the invention. In an embolization device according to the fifth embodiment, as shown in FIG. 18A, a clip-shaped fixing portion 122 is provided at one end of a placing object 121 for embolizing the bronchus H4 in the state of adhering closely to the internal cavity of the bronchus H4. This fixing portion 122 serves to fix the placing object 121 to the wall of the bronchus H4 from the internal cavity of the bronchus H4, and has a clip 123 to be hooked on, for example, not only the mucosa of a bronchus but also a bronchial cartilage. The clip 123 of the fixing portion 122 has hooks 124 at its leading portion so that it can firmly hold a bronchial cartilage. Incidentally, the fixing portion 122 of the placing object 121 may include a needle-shaped element having a hook, instead of the clip 123.

In the fifth embodiment, since the fixing portion 122 is positioned at the bronchial bifurcation H4*b* of the bronchus cartilage as shown in FIG. 18B, the placing object 121 can be fixed easily and safely. Even in the case where the fixing portion 122 is made of a needle having a hook, the fixing portion 122 can be comparatively safely made to puncture the bronchial bifurcation H4*b*.

A holding element, like depicted in FIG. 1, is used to fix the clip 123 at the bronchial bifurcation. The holding element holds the clip 123 and carries it to the bifurcation. When the clip 123 is located at the bifurcation, the holding element applies force to deform the clip 123 so that the hooks 124 of the clip 123 bite the bronchial mucosa and cartilage. The placing object should be expandable one as shown in FIGS. 11B, 11C and 11D, because the view and the space for the operation are required.

Consequently, even with the fifth embodiment, it is possible to achieve an advantage similar to that of the first embodiment. Moreover, in the fifth embodiment, it is possible to simplify the construction of the embolized portion of the placing object 121.

Figure 19A:
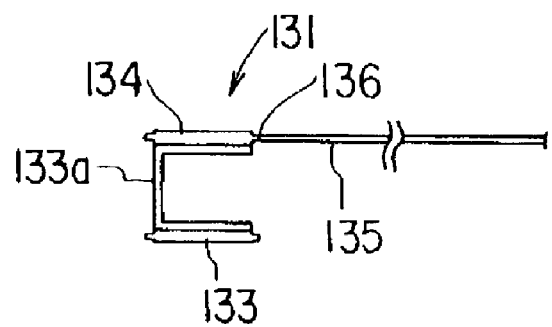
FIGS. 19A and 19B show a sixth embodiment of the invention, FIG. 19A being a longitudinal sectional view of the essential portions, showing the state in which a balloon is attached to a side surface of a transparent cap, and FIG. 19B being a longitudinal sectional view of the essential portions, showing the state in which the transparent cap of a placing object is fitted on a leading portion of an endoscope.
Figure 19B:
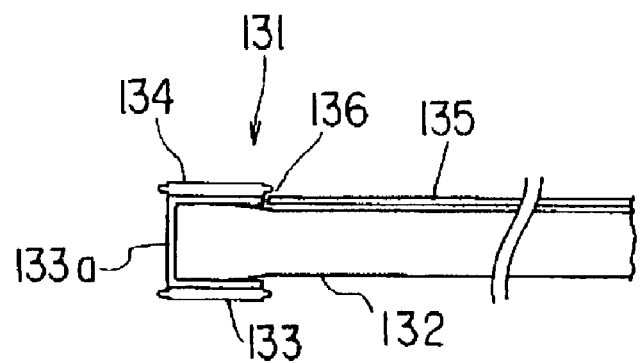

FIGS. 19A, 19B and 20 show a sixth embodiment of the invention. A placing object 131 of the sixth embodiment is made of a transparent cap 133 having a diameter, which enables the placing object 131 to be fitted onto a leading portion of an endoscope 132, such as a bronchoscope. A leading portion of the transparent cap 133 is an embolization element 133*a*. In the sixth embodiment, as shown in FIG. 19B, the transparent cap 133 is secured in the state of being fitted on the leading portion of the bronchoscope 132, and a delivery device for a bronchus embolization element is configured with the bronchoscope 132. The transparent portion of the transparent cap 133 may be made of a material such as polysulphone, polyethylene, polypropylene or poly methyl methacrylate (PMMA).

For example, an expandable balloon 134 is attached to the peripheral surface of the transparent cap 133 as shown in FIG. 19A. The leading portion of a small-diameter catheter 135 is connected to the balloon 134. A proximal portion of the catheter 135 is disposed to extend to an operator side. Thus, a substance can be injected from the operator side into the internal cavity of the balloon 134 through the catheter 135. Incidentally, a cutting mechanism 136 for cutting the balloon 134 from the placing object 131, such as the heating element 77 shown in FIGS. 13A and 13B, is provided at a leading portion of the catheter 135.

The transparent cap 133 of the placing object 131 of the sixth embodiment is fitted onto the leading portion of the endoscope 132 as shown in FIG. 19A, and is inserted into the internal cavity of the target bronchus H4 as shown in FIG. 20. At a time when the leading portion of the endoscope 132 reaches the target part, a substance, such as physiological saline, air or water, is injected into the internal cavity of the balloon 134 by the use of the catheter 135 or the like, to expand the balloon 134. Thus, the placing object 131 embolizes the bronchus H4 with the peripheral surface of the placing object 131 adhering closely to the wall of the bronchus H4. After that, the catheter 135 is cut from the placing object 131, whereby the placement of the placing object 131 is completed. After the catheter 135 is cut, the balloon 134 is sealed by heat as shown in FIGS. 13A and 13B.

Consequently, in the sixth embodiment, the placing object 131 can be inserted into the internal cavity of the target bronchus H4 by the bronchoscope 132 and the bronchus H4 can be embolized by the placing object 131. Therefore, even with the sixth embodiment, it is possible to achieve an advantage similar to that of the first embodiment (refer to FIGS. 1A to 1C and 4).

In addition, in the sixth embodiment, since the endoscope 132 can be used as a delivery device for the bronchus embolization device, there is no need for a special delivery device. Moreover, since the placing object 131 is formed by the transparent cap 133 that is fitted onto the leading portion of the endoscope 132, there is also an advantage which prevents the field of view of the endoscope 132 from being hindered during the insertion of the endoscope 132.

A construction that does not use the catheter 135 may also be adopted. In this construction, the kind of element to be attached to the peripheral side of the transparent cap 133 may not be the balloon 134, and may also be an expansive material which expands by absorbing water or any other fluid, for example, a water absorptive polymer material or a material such as sponge which holds a compressed shape when it is dry. In this case, the transparent cap 133 is inserted into the bronchus in the state being fitted on the bronchoscope 132, and after having been guided to a target position, the water absorptive material expands to reliably fix the transparent cap 133 to the wall of the bronchus. During this state, the bronchoscope 132 is drawn out. Moreover, the part of the peripheral surface of the transparent cap 133 that comes into contact with the wall of the bronchus may also be formed of a biocompatible material such as silicone.

In the case of this construction, there is no need for the catheter 135 for expanding a contact element made of an expansive material which forms part of the peripheral surface of the transparent cap 133, and the transparent cap 133 can be inserted into as thin a bronchus as possible in the state of being attached to the leading portion of the endoscope 132 and the placing object 131 can be placed to adhere closely to the wall of the bronchus.

In the case of the endoscope 132 having a channel, as positive means for removing at a placement part the placing object 131 fitted on the leading portion of the endoscope 132, there is also a method of injecting a fluid such as a liquid or a gas through the channel of the endoscope 132 and increasing the pressure between the placing object 131 and the endoscope 132 to thereby force the placing object from the leading portion of the endoscope 132.

FIGS. 21A and 21B show a seventh embodiment of the invention. The seventh embodiment is a modification of the placing object 131 of the sixth embodiment (refer to FIGS. 19A and 19B and 20).

Specifically, the seventh embodiment is provided with a placing object 143 which includes a coil 141 and a thin transparent film 142 stuck to surround the coil 141, instead of the placing object 131 made of the transparent cap 133 in the sixth embodiment.

Furthermore, the seventh embodiment is provided with a sheath 144 which is used in the state of being fitted on the bronchoscope 132. This sheath 144 includes a leading sheath 144a which covers the periphery of the leading portion of the bronchoscope 132, and an elongated manipulation sheath 144b which can project from and retract into the leading sheath 144a. A placing object accommodation portion 145 into which to accommodate the placing object 143 is formed between the leading sheath 144a and the leading portion of the bronchoscope 132.

As shown in FIG. 21A, when the manipulation sheath 144b is in the state of being held at a retracted position where the manipulation sheath 144b is retracted from the placing object accommodation portion 145, the placing object 143 can be accommodated in the placing object accommodation portion 145. During this state, the placing object 143 is stored in the placing object accommodation portion 145 at a leading portion of the sheath 144, and is attached to the peripheral surface of the leading portion of the bronchoscope 132.

During this state, as shown in FIG. 21B, when the manipulation sheath 144b is manipulated to be pushed out toward the leading end of the bronchoscope 132, the placing object 143 accommodated in the placing object accommodation portion 145 is pushed out toward the leading end, whereby the placing object 143 can be pushed out of the placing object accommodation portion 145. In this construction, if a material, such as memory metal, which has the property of restoring its shape to a particular one is used for the coil 141 of the placing object 143, the placing object 143, when it is pushed out of the placing object accommodation portion 145, can be expanded to a shape larger in diameter than when the placing object 143 is positioned in the sheath 144.

The placing object 143 of the seventh embodiment is inserted into the internal cavity of the target bronchus H4 in the state of being accommodated in the placing object accommodation portion 145 at the leading portion of the sheath 144 and being attached to the peripheral surface of the leading portion of the bronchoscope 132. At a time when the leading portion of the endoscope 132 reaches the target part, the manipulation sheath 144b is manipulated to be pushed out toward the leading end of the bronchoscope 132, whereby the placing object 143 accommodated in the placing object accommodation portion 145 is pushed out toward the leading end of the bronchoscope 132. Thus, the placing object 143 embolizes the bronchus H4 with the peripheral surface of the placing object 143 adhering closely to the wall of the bronchus H4.

Consequently, in the seventh embodiment, the placing object 143 can be inserted into the internal cavity of the target bronchus H4 by the bronchoscope 132 and the bronchus H4 can be embolized by the placing object 143. Therefore even with the seventh embodiment, it is possible to achieve an advantage similar to that of the first embodiment (refer to FIGS. 1A to 1C and 4).

In the seventh embodiment, similarly to the case of the sixth embodiment, since the bronchoscope 132 can be used as a delivery device for the bronchus embolization device, there is no need for a special delivery device. Incidentally, if a material, such as memory metal, which has the property of restoring its shape to a particular one is used for the coil 141 of the placing object 143, the placing object 143, when it is pushed out of the placing object accommodation portion 145, can expand to a shape larger in diameter than when the placing object 143 is positioned in the sheath 144. Therefore, it is possible to embolize a bronchus having a large inside diameter.

FIGS. 22A and 22B show an eighth embodiment of the invention. The eighth embodiment is provided with a placing object 151 made of a shape memory material such as memory metal. This placing object 151 can be deformed into a first shape which is a linear shape of a shaft portion 152 as shown in FIG. 22A, and into a second shape which is a ring- or coil-like shape into which the shaft portion 152 is deformed as shown in FIG. 22B. The placing object 151 of the eighth embodiment can be deformed into the first shape by an external force obtained as by being inserted into and confined within a thin tube. When there is no external force, the placing object 151 is held in the second shape. In addition, a thin film 153 is attached to the shaft portion 152 of the placing object 151 along the longitudinal axis of the shaft portion 152.

The placing object 151 of the eighth embodiment can pass through the channel of a thin catheter or an endoscope in the state of being deformed into the first linear shape as shown in FIG. 22A. The placing object 151 is accordingly inserted into the bronchus in the first shape.

After the placing object 151 passes through the channel of the thin catheter or the endoscope in the state of being deformed in the first shape, the placing object 151 is pushed out of the channel of the thin catheter or the endoscope within the bronchus, so that an external force which acts on the shaft portion 152 of the placing object 151 is removed. In this case, the shaft portion 152 of the placing object 151 is restored to the second shape. When the shaft portion 152 of the placing object 151 is in the state of being restored to the second shape as shown in FIG. 22B, the thin film 153 attached to the shaft portion 152 overlap each other in the central portion of the shaft portion 152 which is deformed in a ring- or coil-like shape, thereby embolizing the bronchus.

Consequently, in the eighth embodiment, the placing object 151 is made to pass through the channel of a thin catheter or an endoscope with the shaft portion 152 deformed in the first linear shape as shown in FIG. 22A, and is inserted into the internal cavity of the target bronchus H4. In the internal cavity of the bronchus H4, the shaft portion 152 of the placing object 151 is restored to the second shape as shown in FIG. 22B, whereby the bronchus H4 can be embolized by this placing object 151. Therefore, even with the eighth embodiment, it is possible to achieve an advantage similar to that of the first embodiment (refer to FIGS. 1A to 1C and 4).

In addition, in the eighth embodiment, it is possible to retrieve the placing object 151 placed temporarily, by holding the placing object 151 with forceps or the like for the bronchoscope and drawing the placing object 151 into the channel of the endoscope to form the placing object 151 into the first shape.

Incidentally, the thin film 153 attached to the shaft portion 152 of the placing object 151 may be adhered to the shaft portion 152 by fusion bonding with heating or by an biocompatible adhesive such as fibrin adhesive.

In addition, the part of the shaft portion 152 that appears on an external circumferential side when the shaft portion 152 of the placing object 151 is restored to the second shape may also have a stopper such as a projection being formed so that the placing object 151 is prevented from coming off or vibrating after having been placed in the bronchus.

In seventh and eighth embodiments, memory metals are used by way of example only, alternative materials include stainless steel wire for springs and piano wire. FIG. 23 shows a ninth embodiment of the invention. The ninth embodiment is provided with a placing object 161 made of a biocompatible material which can assume two different forms, liquid and solid. Examples of a material having such a property are blood, resins that polymerize by rays such as ultraviolet rays, and silicone resins which change from liquid to solid by mixing with curing agents.

Furthermore, the embolization device of the ninth embodiment is provided with a catheter 162 for injecting a liquid placing object 161 into the internal cavity of the bronchus H4. This catheter 162 is inserted into, for example, a channel 164 of a bronchoscope 163, and is inserted into the internal cavity of the bronchus H4 through the channel 164 of the bronchoscope 163.

In addition, one or a plurality of catheters 162 may be provided according to the properties of the placing object 161. Furthermore, the bronchoscope 163 is provided with a light guide 165 or the like for sending light from an external light source to a local portion. Incidentally, in the case of the bronchoscope 163 having a construction provided with a light source at its leading portion, the light guide 165 may also be omitted.

In the embolization device of the ninth embodiment, as shown in FIG. 23, the catheter 162 is inserted into the internal cavity of the bronchus H4 through the channel 164 of the bronchoscope 163, and the liquid placing object 161 is injected into the internal cavity of the bronchus H4 through the catheter 162. At this time, the placing object 161 injected into the internal cavity of the bronchus H4 is solidified to embolize the bronchus H4. The placing object 161 injected into and solidified in the internal cavity of the bronchus H4 penetrates into the bronchus H4 to be embolized as well as a bronchus internal cavity which is located at the periphery of the bronchus H4 and has a complicated shape. Therefore, there is no need for a special construction for preventing the placing object 161 from coming off.

In addition, from the moment when the placing object 161 is injected until the solidification of the placing object 161 is completed, an embolization object for preventing a back flow may be placed in an embolization target part so that the liquid placing object 161 is prevented from flowing into any location other than the embolization target part.

In the ninth embodiment, the catheter 162 is inserted into the internal cavity of the bronchus H4 through the channel 164 of the bronchoscope 163, and after the liquid placing object 161 is injected into the internal cavity of the target bronchus H4 through the catheter 162, the bronchus H4 can be embolized by the solidified placing object 161. Therefore, the ninth embodiment has an advantage similar to that of the first embodiment (refer to FIGS. 1A to 1C and 4).

In addition, since the ninth embodiment uses the liquid placing object 161, the ninth embodiment can be used irrespective of the shape of a target bronchus to be embolized. In addition, the ninth embodiment has the advantage that manipulating techniques become easy.

Incidentally, the placing object 161 and the delivery device may also have structures that allow a guide wire to pass through them.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A method of treating lung emphysema, lung tuberculosis, bronchus tuberculosis and other lung diseases by embolization, the method comprising:
    directing a resilient embolization object into a bronchus/bronchiole of one of subject; and
    placing the embolization object in a bifurcation of the bronchus or the bronchiole by bending the embolization object in a middle portion and inserting each end of the embolization object into a respective branch of the bifurcation to enhance the placement performance of the embolization object.

2. A method of embolizing an internal cavity of at least one of a bronchus and a bronchiole of a subject, comprising:
    carrying a resilient placing object by means of a delivery device to a bifurcation of one of the bronchus and the bronchiole of the subject, the bifurcation having at least a first branch tubular cavity and a second branch tubular cavity;
    deforming the placing object according to a relative angle between the first branch tubular cavity and the second branch tubular cavity, and inserting a first end of the placing object into the first branch tubular cavity and a second end of the placing object into the second branch tubular cavity for embolization; and
    leaving the placing object in the bifurcation and removing the delivery device from the subject.

* * * * *